United States Patent [19]

Scharf et al.

[11] Patent Number: 4,530,785

[45] Date of Patent: Jul. 23, 1985

[54] PROCESS FOR THE PURIFICATION OF MICROBIAL PROTEIN ISOLATES

[75] Inventors: Udo Scharf, Kelkheim; Merten Schlingmann, Königstein, both of Fed. Rep. of Germany

[73] Assignee: Hoechst Aktiengesellschaft, Frankfurt am Main, Fed. Rep. of Germany

[21] Appl. No.: 601,697

[22] Filed: Apr. 18, 1984

[30] Foreign Application Priority Data

Apr. 20, 1983 [DE] Fed. Rep. of Germany ....... 3314292

[51] Int. Cl.$^3$ ................................................ A23J 1/18
[52] U.S. Cl. ............................... 260/112 R; 426/656; 426/429; 426/431
[58] Field of Search ..................... 260/112 R

[56] References Cited

U.S. PATENT DOCUMENTS

| | | | |
|---|---|---|---|
| 3,725,075 | 4/1973 | Muroi et al. | 260/112 R |
| 3,781,264 | 12/1973 | Akin | 260/112 R |
| 3,784,536 | 1/1974 | Akin et al. | 260/112 R |
| 3,819,610 | 6/1974 | Akin | 260/112 R X |
| 3,833,552 | 9/1974 | Akin | 260/112 R |
| 3,885,050 | 5/1975 | Ridgway, Jr. et al. | 426/60 |
| 3,891,772 | 6/1975 | Ridgway, Jr. et al. | 426/60 |
| 3,962,466 | 6/1976 | Nakabayashi | 260/112 R X |
| 3,996,104 | 12/1976 | Lindblom et al. | 260/112 R X |
| 4,133,904 | 1/1979 | Steer et al. | 260/112 R X |
| 4,135,000 | 1/1979 | Schuldt, Jr. | 260/112 R X |
| 4,206,243 | 6/1980 | Schlingmann et al. | 260/112 R X |
| 4,330,464 | 5/1982 | Lawford et al. | 260/112 R |
| 4,341,802 | 7/1982 | Hopkins | 260/112 R X |
| 4,472,302 | 9/1984 | Karkhanis | 260/112 R |

OTHER PUBLICATIONS

Biotechnology & Bioengineering, "Reduction of the Nucleic Acids Content of Single Cell Protein Concentrates," vol. XIV, pp. 447–457.
Biotechnology & Bioengineering, "A Method for Large Reduction of the Nucleic Acid Content of Yeast," vol. XIV, pp. 173–177 (1972).
Annual Reports on Fermentation Processes, vol. 1, Academic Press (1977).

*Primary Examiner*—Howard E. Schain
*Attorney, Agent, or Firm*—Finnegan, Henderson, Farabow, Garrett & Dunner

[57] ABSTRACT

Substances producing an undesired odor and taste can be removed from microbial protein materials if these materials are treated with aqueous solutions which contain a phosphate and/or a hydrophilic low molecular weight aliphatic compound which contains at least two functional groups from the series comprising hydroxy, formyl, keto and carboxy. Preferred aliphatic extraction auxiliaries are flavoring acids, sugars and polyols, and phosphates are orthophosphates and diphosphates. The extraction can also be carried out in association with reducing the nucleic acid content of defatted cell aggregates.

18 Claims, No Drawings

PROCESS FOR THE PURIFICATION OF MICROBIAL PROTEIN ISOLATES

German Offenlegungsschrift No. 2,173,038 discloses the extraction of substances which have an unpleasant odor and taste from unicellular protein materials, especially yeasts and bacteria, by extraction with an aqueous solution which contains 60 to 80% by volume of a lower aliphatic alcohol.

German Pat. No. 2,633,666 discloses the reduction of the content of lipids and nucleic acids in microbial cell aggregates by treating, in a first step, these cell aggregates with an extraction mixture composed of ammonia and a polar solvent from the series comprising the lower alkanols, lower glycols and the methyl or ethyl ethers of a lower glycol, the maximum total water content being 30% by weight relative to the amount of solvent, and the concentration of ammonia advantageously being 1 to 10% by weight, likewise relative to the solvent, and then treating the residue of the cell aggregates with water. In this process, the lipids and a major part of the substances producing the odor and taste are extracted by the extraction mixture, while the nucleic acids are removed by the water treatment, which can be carried out in one step or several steps. The protein isolate thus obtained is then essentially free of odor and taste and can be used directly for many applications, including food for humans.

However, in practice, it is not always possible to prevent an unpleasant odor and/or taste from still adhering to protein isolates of this type, and this particularly interferes with specific applications. Extraction with an aqueous aliphatic alcohol in accordance with German Offenlegungsschrift No. 2,137,038 is ineffective in these cases.

It has now been found that substances producing an undesired odor and taste can be removed from microbial protein isolates if these isolates are treated with aqueous solutions which contain a phosphate and/or a hydrophilic low molecular weight aliphatic compound which contains at least two functional groups from the series comprising hydroxy, formyl, keto and carboxy. Preferred embodiments of this invention are illustrated in detail below.

Suitable "low molecular weight" aliphatic compounds are primarily those which contain a carbon chain of 2 to 6 carbon atoms, or, in the case of disaccharides and oligosaccharides, two or more of these units.

Since the protein isolates or the functionalised derivatives prepared from them are intended for food for humans, compounds of low toxicity will be employed as auxiliaries for the extraction according to the invention. For this reason, physiologically acceptable materials are preferred, that is to say flavoring acids, sugars and polyols, such as glycerol and sugar alcohols, for the aliphatic compounds. However, if it is possible to remove the material readily and virtually quantitatively from the protein isolate, it is also possible to use other auxiliaries such as, for example, oxalic acid, since the residual amounts remaining are then far below the limit of acceptability.

Suitable phosphates are orthophosphates, oligophosphates and polyphosphates, and long-chain and cyclic polyphosphates are possible. Orthophosphates and diphosphates are preferred, especially in the form of the readily soluble sodium and potassium salts.

The aliphatic compounds having acid reactions are advantageously used in the form of their alkaline earth salts and, in particular, their alkali metal salts. In addition to oxalic acid which has already been mentioned, glycolic acid, glyoxylic acid, pyruvic acid, fumaric acid, succinic acid, tartaric acid, ascorbic acid, especially lactic acid, citric acid and malic acid, as well as sugar acids from the aldonic, aldaric and uronic series, and the corresponding lactones, especially gluconic acid δ-lactone, are preferred.

Furthermore, sugars are advantageous extraction auxiliaries, namely, from the monosaccharide series, the aldoses and ketoses of the pentose and hexose series, especially glucose and fructose, of the disaccharides especially sucrose, and of the oligosaccharides especially products of hydrolysis of starch, such as starch syrup.

In addition to glycerol which has already been mentioned, suitable aliphatic compounds which contain only hydroxy groups as the functional groups include erythritol, pentaerythritol and, in particular, sugar alcohols, especially sorbitol.

Mixtures of these extraction auxiliaries are also advantageous, for example a phosphate combined with an aliphatic compound, such as sucrose, or a mixture of aliphatic compounds, for example glyoxylic acid containing oxalic acid, or a sugar alcohol/sugar mixture.

The purification according to the invention can be carried out subsequent to the process according to German Pat. No. 2,633,666. However, it is particularly advantageous if the extraction auxiliaries are added during the nucleic acid extraction. In the case of a multistep nucleic acid extraction, the extraction auxiliary according to the invention can be added to the first step, to a subsequent step or to several steps.

The treatment according to the invention can take place in the range from about 0 to 100° C., advantageously at about 20° to 90° C., and especially at 40° to 80° C. In multi-step processes it is possible for the temperature to be the same or different in each step.

Depending on the purpose for which the protein material is to be used, it is possible for large or small residual amounts of the extraction auxiliary to remain in the protein residue, for example a sugar, when the protein is processed in sweet foodstuffs, such as drinks, bakery products or desserts, or a phosphate when it is intended to use the protein in meat or sausage products, cheese or cheese-like products or (other) spreads for bread.

The lower limit of the content of phosphate and or aliphatic compound in the aqueous solutions is determined by the efficacy while, in principle, the upper limit is only determined by the solubility, since, as pointed out above, it is quite possible in many cases for residual amounts of the extraction agent to remain in the product after extraction. In general, the selected concentrations of auxiliary are from 0.1 to 3, preferably 0.2 to 2, and especially 0.5 to 1, % by weight.

It is self-evident that it is also possible to apply the purification process according to the invention to other proteins, for example to chemically modified microbial proteins.

The invention is illustrated in detail in the examples which follow. In these, percentage data relate to weight.

EXAMPLE 1

100 g of spray-dried protein isolate according to Example 1 of German Pat. No. 2,633,666 are introduced, with stirring, into a solution of 5 g of sucrose in 1 liter of water. The suspension is heated to 80° C. and stirring is continued at this temperature for half an hour. Then the protein isolate is removed from the extraction solution by centrifugation and is dried.

The microbial protein isolate thus obtained is distinguished by improved taste and odor. The composition of the protein constituents is the same as before the extraction.

EXAMPLE 2

Example 1 is repeated with the modification that the solid which has been removed by centrifugation is again thoroughly stirred with 1 liter of water in order to remove adherent sucrose. After centrifuging again, the protein isolate is dried. It likewise has an improved odor and taste and has the same aminoacid composition as before the extraction.

EXAMPLE 3

The starting material is a defatted cell aggregate according to Example 1 of German Pat. No. 2,633,666 which still contains the nucleic acids. 90 g of this cell aggregate are suspended in 900 ml of a 0.5% strength sucrose solution, the suspension is heated to 55° C. and stirring is continued at this temperature for 20 minutes. After cooling to 30° C., the suspension is centrifuged. 900 ml of water are added to the resulting sediment and the mixture is stirred at 20° C. for 10 minutes. It is then centrifuged again and the sediment is dried under reduced pressure.

Compared with a product according to Example 1 of German Pat. No. 2,633,666, the product is distinguished by an improved odor and taste. The nucleic acid and aminoacid composition are identical.

EXAMPLE 4

Example 2 is repeated, but a 0.5% strength solution of disodium orthophosphate is employed in both extraction steps. A product having an improved odor and taste and unchanged aminoacid composition is likewise obtained.

EXAMPLE 5

Example 1 is repeated, but the sucrose is replaced by sorbitol. A product of comparable quality is obtained.

EXAMPLES 6-8

The procedure is as in Example 1, but the sucrose is replaced by lactic acid, malic acid or tartaric acid, and products of comparable quality are obtained.

EXAMPLES 9-11

If the procedure is as in Example 3, but the sucrose is replaced by lactic acid, starch syrup or glycerol, then products of comparable quality are obtained.

EXAMPLE 12

If the procedure is as in Example 3, but a 0.5% strength solution of sodium diphosphate is employed in both extraction steps, then a product having an improved odor and flavor and of unchanged aminoacid composition is likewise obtained.

EXAMPLE 13

If the procedure is as in Example 2, but lactic acid is employed in the first step and the pH is adjusted to 6-7 with sodium hydroxide solution, and then the sucrose solution is used in the second step, then a product having an improved odor and taste and of unchanged aminoacid composition is obtained.

EXAMPLE 14

If the procedure is as in Example 3, but the extraction agents mentioned in Example 13 are used, then a comparable product is likewise obtained.

Appendix: Example 1 of German Pat. No. 2,633,666:

Methylomonas clara ATCC 31,226 was cultured under aerobic conditions in a nutrient solution containing methanol as the only source of carbon, ammonia as the only source of nitrogen, phosphate, iron and magnesium salts and other customary trace elements. The bacterial cell aggregate produced thereby was removed from the solution and subjected to spray-drying.

300 g of methanol were added to 100 g of this cell aggregate. While stirring the suspension, 10 g of $NH_3$ gas were passed in and dissolved. The temperature while the gas was passed in was maintained at 25° C.–35° C. by cooling. The mixture of methanol, ammonia and cell aggregate was stirred at 20° C. for 30 minutes.

To separate the solid and liquid phases, the mixture was filtered and the solid residue was washed once with 300 ml of methanol. After renewed filtration, both filtrates were combined. This brown solution contained the lipids in the starting material employed. Methanol and ammonia were removed by vacuum distillation (100 Torr, 40° C.). The residue, which amounted to 9.5% by weight of the cell material employed, was a dark-brown paste with an unpleasant odor and was composed of free fatty acids, glycerides, phospholipids and secondary metabolites.

The solid residue, obtained on filtration, of the extracted cell aggregate was dried at 40° C. in vacuo (100 Torr) for 5 hours. 90 g of defatted cell aggregate were thus obtained, and this was free of odor and had a lighter color than the starting material.

To reduce the content of nucleic acids, this cell aggregate was suspended in 900 ml of water. When the suspension had been homogenised by stirring, its pH was 6.9.

After increasing the temperature to 55° C., it was stirred for a further 20 minutes, then cooled to 30° C. and separated into solid and liquid phases by centrifugation. The resulting sediment was again mixed with 900 ml of water and stirred at 20° C. for 10 minutes. It was then again centrifuged and the sediment was dried under reduced pressure.

The yield was 65 g. The content of nucleic acids had decreased from the original 11.2% to 1.5%, and the fat content had decreased from 7% to 0.8%. The product was free of odor in the dry state, while it had a pleasant odor when moistened with water.

Addendum

German Pat. No. 2,633,666 referred to above corresponds to U.S. Pat. No. 4,206,243 which hereby is incorporated by reference.

We claim:

1. A process for the purification of microbial protein isolates, which comprises treating defatted microbial cells by suspending the defatted microbial cells in an aqueous solution of a phosphate and/or a hydrophilic low molecular weight aliphatic compound which contains at least two radicals selected from the group consisting of hydroxy, formyl, keto and carboxy and isolating the protein residue.

2. The process as claimed in claim 1, wherein the microbial protein isolates are defatted cell aggregates still containing nucleic acids.

3. The process as claimed in claim 1, wherein the treatment is carried out in more than one step in which steps the extraction agent is the same or different.

4. The process as claimed in claim 1, wherein the phosphate is a sodium or potassium orthophosphate or diphosphate.

5. The process as claimed in claim 1, wherein an aliphatic compound having an acid reaction is employed in the form of its alkaline earth or alkali metal salt.

6. The process as claimed in claim 1, wherein the isolates are treated with aqueous solutions of a flavoring acid, a sugar or a polyol.

7. The process as claimed in claim 1, wherein the aqueous solution contains lactic acid, malic acid or citric acid.

8. The process as claimed in claim 1, wherein the treatment is carried out in a first step with lactic acid, and in a subsequent step with sucrose solution.

9. The process as claimed in claim 1, wherein the treatment is carried out at about 0° to 100° C.

10. The process as claimed in claim 1, wherein the treatment is carried out at 20° to 90° C.

11. The process as claimed in claim 1, wherein the treatment is carried out at 40° to 80° C.

12. The process as claimed in claim 1, wherein the aqueous solution contains 0.1 to 3% by weight of phosphate or said hydrophilic compound.

13. The process as claimed in claim 12, wherein the concentration is 0.2 to 2%.

14. The process as claimed in claim 12, wherein the concentration is 0.5 to 1%.

15. A purified microbial protein isolate obtained as claimed in claim 1.

16. A foodstuff or foodstuff additive containing a protein isolate as claimed in claim 15.

17. A process for the purification of microbial protein isolates which comprises suspending defatted microbial cells in an aqueous solution containing an effective amount of a hydrophilic low molecular weight flavoring acid to improve the odor or taste of the cells; maintaining the cells in the solution at a temperature and for a time sufficient to improve the odor or taste of the cells; and isolating the protein residue.

18. A process according to claim 17, wherein the acid is selected from the group consisting of lactic acid, malic acid and citric acid.

* * * * *